United States Patent
Tomellini et al.

[11] Patent Number: 5,380,281
[45] Date of Patent: Jan. 10, 1995

[54] DEVICE FOR THE ADMINISTRATION OF DRUGS, PARTICULARLY TWO-COMPONENT DRUGS

[75] Inventors: Giorgio Tomellini; Gian A. Rollandi, both of Genova, Italy

[73] Assignee: BRACCO, S.p.A., Milano, Italy

[21] Appl. No.: 133,014

[22] PCT Filed: Apr. 6, 1992

[86] PCT No.: PCT/EP92/00777
§ 371 Date: Jan. 13, 1994
§ 102(e) Date: Jan. 13, 1994

[87] PCT Pub. No.: WO92/18177
PCT Pub. Date: Oct. 29, 1992

[30] Foreign Application Priority Data
Apr. 9, 1991 [IT] Italy ................. TO91 U 000078

[51] Int. Cl.6 ............ A61M 37/00; A61M 5/24; A61M 5/28; A61B 19/00
[52] U.S. Cl. .................. 604/85; 604/88; 604/203; 604/411
[58] Field of Search ............ 604/82–88, 604/201, 203, 205, 411, 414–416

[56] References Cited
U.S. PATENT DOCUMENTS

| | | | |
|---|---|---|---|
| 3,405,712 | 10/1968 | Pierick | 604/88 |
| 3,500,830 | 3/1970 | Eck | 128/218 |
| 3,659,602 | 5/1972 | Cloyd | 604/88 |
| 3,739,780 | 6/1973 | Ogle | 604/203 |
| 3,768,474 | 10/1973 | Burke et al. | 128/220 |
| 3,994,296 | 11/1976 | Cloyd | 128/220 |
| 4,180,070 | 12/1979 | Genese | 604/414 |
| 4,994,029 | 2/1991 | Rohrbough | 604/88 |

FOREIGN PATENT DOCUMENTS

| | | | |
|---|---|---|---|
| 1167766 | 11/1958 | France | 604/82 |
| 9003505 | 6/1990 | WIPO | |

*Primary Examiner*—C. Fred Rosenbaum
*Assistant Examiner*—Frank Wilkens, III
*Attorney, Agent, or Firm*—Edward D. Manzo; Ted K. Ringsred

[57] ABSTRACT

The device comprises a tubular housing with two jackets and a container filled with the liquid component of a drug. Within the inner jacket of the housing, close to the closed end thereof, is a chamber containing the powdered components of a drug. A needle for piercing the stopper which closes the container enables the interior of the container to be put in communication with the chamber so as to allow the liquid component to flow out and consequently mix with the powdered component. The subsequent advance of the container into the housing, with the consequent penetration of the piston into the container, causes the further flow of the liquid component into the chamber carrying the drug solution to the exterior of the device generally like a syringe. Its use as a supplier of infusions is also foreseen.

9 Claims, 1 Drawing Sheet

DEVICE FOR THE ADMINISTRATION OF DRUGS, PARTICULARLY TWO-COMPONENT DRUGS

BACKGROUND OF THE INVENTION

The present invention relates to devices for the administration of drugs.

More particularly, the present invention constitutes an improvement in the solution described in the prior Italian Industrial utility model application 15156-B/89 and the corresponding DE-U-9 003 505.

The application in question relates to a device for the administration of drugs, particularly liquids, comprising a double-walled housing which is open at one end and closed at the other by an end wall, in which a needle is fixed and extends substantially the entire length of the housing. The inner jacket of the housing is threaded at least at its open end so as to receive a threaded spigot of a piston applied in the form of a stopper to the open end of a cylindrical container housing the liquid to be administered. The piston has an axial bore closed by a diaphragm which can be pierced by the needle when the spigot of the piston is screwed into the inner jacket. By forming the cylindrical container axially into the said housing it is possible to supply the said liquid product. The entirety is generally like a syringe; it is also possible to envisage the use of this same structure as a device for supplying infusions.

The present invention attempts principly to improve on this prior solution so as to extend its use to the supply of drugs constituted by a liquid and a powder which must be dissolved in the liquid before use. At present the usual method used with drugs of this type provides for a liquid to be drawn up from a phial into a syringe and then for the liquid to be injected into another phial containing the powdered drug and then—after the drug has dissolved—for the solution to be taken up again in a syringe before the injection proper can be effected: a sequence of operations which is rather complicated and must be carried out with extreme care.

According to the present invention, the object is achieved by means of a device for the administration of drugs having the characteristics claimed specifically in the claims which follow.

BRIEF DESCRIPTION OF THE DRAWINGS

The invention will now be described, purely by way of non-limiting example, with reference to the appended drawings; in which.

DETAILED DESCRIPTION OF THE PREFERRED EMBODIMENT

Figure 1:
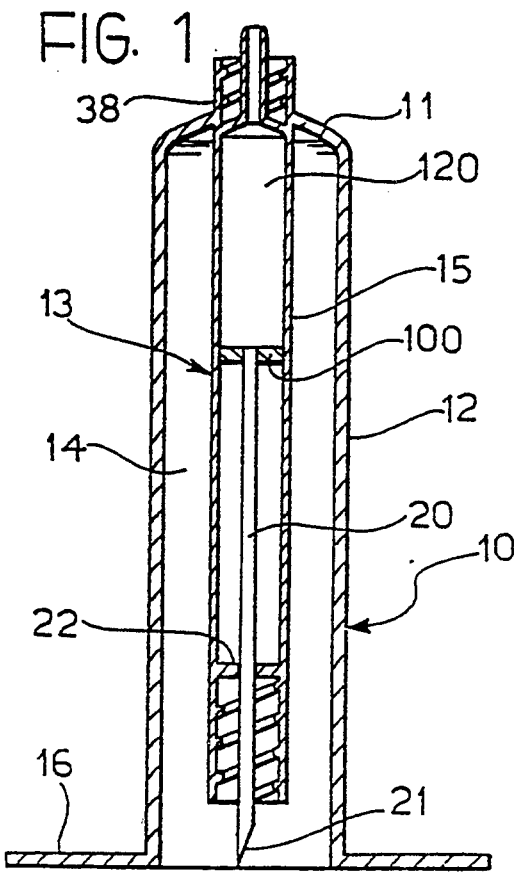
FIG. 1 is an axial section through a housing of a device according to the invention.
Figure 3:
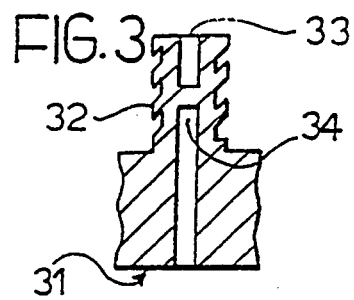
FIG. 3 shows one of the elements of the container of FIG. 1 in greater clarity.

In its essentials and in its basic characteristics of use, the device of the invention does not differ substantially from the device which is the subject of the prior application 15156-B/89 (and DE-U-9 003 505) to which reference has already been made.

In particular, FIGS. 1 to 4 of the drawings appended hereto correspond to FIGS. 1 to 4 of the prior application and the same reference numerals are used to indicate identical or equivalent parts to those used in the specification of the prior application.

Thus, reference 10 generally indicates a cylindrical housing having an end wall 11 and two concentric jackets 12 and 13 which define An annular chamber 14 and a central hollow body 15.

Similarly a needle fixed within the inner jacket 13 of the body 10 is indicated 20.

However the solution of the present invention differs from that described in application 15156-B/89 (or DE-U-9 003 505) in that the needle 20 does not extend through the entire length of the housing 10, that is, from the end wall 11 up to the opposite, open end of the housing 10, but only through part of the length of the housing 10 itself: more precisely, it extends through that part which is between an intermediate partition 100 within the jacket 13 and the end of the jacket which is towards the open end of the housing 11.

More particularly, one of the ends of the needle 20 passes through the partition 100 and defines an end chamber 120 within the inner jacket 13 which, in the embodiment illustrated here, occupies about a third of the overall length of the jacket 13 itself. Naturally, this dimensional choice, although preferred for several reasons, should certainly not be considered as limiting.

The chamber 120 is intended to contain the powdered component of the two-component drug (liquid-powder) intended to be injected by the device of the invention.

For the rest, in substantial analogy with the solution described in application 15156-B/89 (or DE-U-9 003 505), the needle 20 terminates at its end opposite the chamber 120 in a pointed end 21 intended to pass through the perforable stopper 31 (illustrated in greater detail in FIG. 3) of the cylindrical container 30 which houses the liquid component of the drug to be injected. Close to the open end of the housing 10, the needle 20 is supported by an intermediate diaphragm 22 beyond which the inner wall of the internal jacket 13 is threaded. The end of the outer jacket 12 has an external flange 16 intended to act as a hand grip for use of the device as a syringe. The container 30 is closed by a piston 31 which, in the original condition in which the container 1 is packaged, is arranged close to the end of the container itself. The piston has a threaded spigot 32 projecting from the container and adapted to be screwed into the threaded end of the inner jacket 13. The piston 31 and the spigot 32 are traversed by an axial bore 33 for receiving the end of the needle 20. In order to seal the container 30, the axial bore 33 is closed in an intermediate position by a diaphragm 34 intended to be pierced by the pointed end 21 of the needle 20. The piston 31, which acts as a stopper for the container 20, is held in a fixed position until the moment of use by a small disc 35 which acts as a stop seal and whose edges are bent over and clamped lightly against the outer surface of the drug container 30. The disc 35 has a central aperture for the sealed passage of the spigot 32. The turned edge of the disc 35 serves as a stop for the annular edge of a cup-shaped cap 36 which serves to protect the spigot 32 and to maintain sterility until the moment at which the drug 30 is supplied.

In general, the housing 11 and the container 30 are supplied as components of a kit or equipment packaged under sterile conditions the administration of two-component drugs, a powdered component (contained in the chamber 120 in the inner jacket 13 of the housing 11) and a liquid component or vector disposed in the container 30, respectively.

At the moment of use, the housing 11 and the container 30 are removed from the kit. After the protective cover 36 has been removed (with tearing of the disc 35), the container 30 is engaged in the housing 10 by the screwing of the spigot 32 into the threaded portion of the inner jacket 13 until the condition illustrated in FIG. 4 has been achieved. More particularly, the peripheral wall or skirt of the container 30, which has radial dimensions intermediate those of the two jackets 12 and 13, is inserted in the annular chamber 14. During the progressive screwing of the spigot 32, the needle 20 penetrates the axial bore 33 until it reaches the diaphragm 34. As the spigot 32 continues to be screwed in, the end 21 of the needle 20 pierces the diaphragm 34 and puts the interior of the container 30 into communication with the interior of the needle 20 and, through the later, with the chamber 120.

Figure 4:
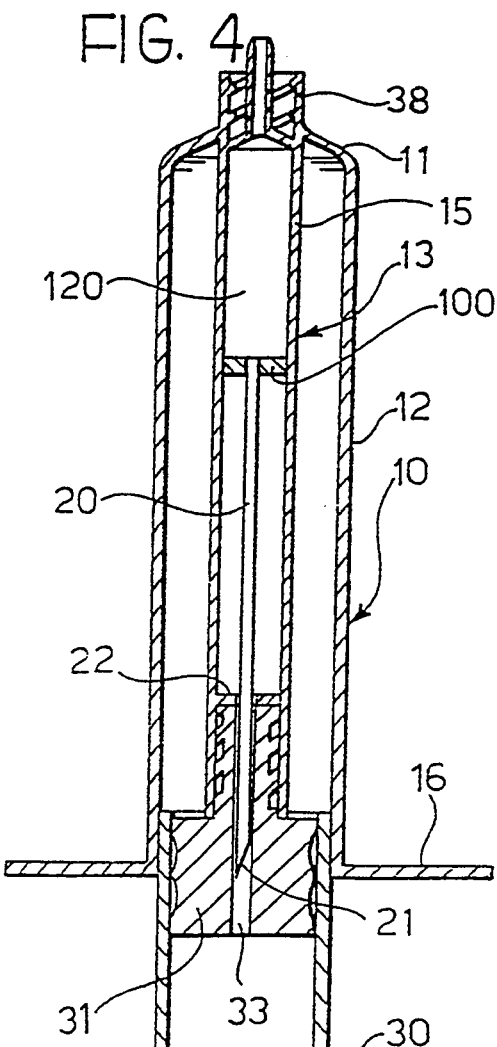
FIG. 4 shows the device of the invention in its condition of use.
Figure 2:
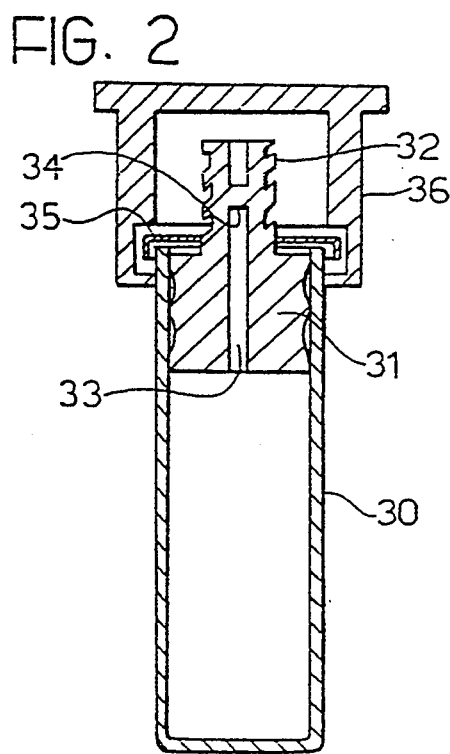
FIG. 2 is an axial section through the container intended to house one of the components, typically the liquid vector of the drug no be supplied.

In these conditions, pressure on the container 30 so as to make in penetrate further into the annular chamber 14, causes the piston 31 to advance into the container 30 with the consequent pumping of the liquid drug component into the chamber 120 which contains the powdered component. When a sufficient quantity of liquid has been made no flow into the chamber 120, the powdered component of the drug can pass into solution, with a mixing process which can be facilitated by the agitation of the assembly formed by the housing 11 and the container 30 interconnected as shown in FIG. 4.

As already seen from the solution of application 15156-B/89 (or DE-U-9 003 505), the end wall 11 of the housing 10 terminates with a spigot 38 in which, or around which, may be arranged the bush or ring nut of a hypodermic needle.

When the hypodermic needle has been fitted onto the spigot 38 and the flanges 16 of the housing 10 are gripped with two fingers, pressure of the thumb on the base of the container 30 causes its further advance into the annular chamber 14 and the consequent, gradual and complete penetration of the piston 31 into the container 30 itself. Thus the liquid component of the drug housed in the container 30 is expelled completely and, passing through the needle 20 into the chamber 120, takes the drug solution formed previously in this chamber with it and enables it to be carried to the exterior through the hypodermic needle mounted on the spigot 30.

The two-component drug may thus be injected in the usual manner of use of a syringe.

Naturally, the solution of the invention may also be used for supplying a tube for infusions. In this case, the housing 10 could usefully be provided with a lateral air take-off for enabling the slow emptying of the drug container 30. In the latter case the sealing disc 35 would not need to be removed and would ensure that the flow of liquid (and of the solution of the drug carried thereby) occurred solely under gravity by virtue of the presence of the aforesaid air take-off.

Naturally, the scope of the present invention extends to models which achieve equal utility by the use of the same innovative concept.

We claim:

1. A device for the administration of drugs, comprising:
    a tubular housing having a double wall including an outer jacket and an inner jacket, said housing being open at one end and closed by an end wall at the opposite end;
    a container for holding a first liquid drug component, said container including a stopper in the form of a slidable piston, said stopper being couplable to the inner jacket of said housing and slidable into said container so as to apply a pressure to the first liquid drug component;
    a chamber formed within said inner jacket adjacent to the end wall of said housing, said chamber for holding a second drug component to be dissolved in said first liquid drug component; and
    a needle mounted within the inner jacket of said housing, said needle having one end opening into said chamber and the opposite pointed end extending toward the open end of said housing, said needle being positioned such that the pointed end perforates an axial bore through said stopper when said stopper is coupled to said inner jacket, so that said container communicates via said needle with said chamber, and when the slidable piston of said container slides into said container said first liquid drug component travels under pressure through said needle into said chamber and mixes with said second drug component.

2. A device according to claim 1, wherein said chamber is defined by said end wall at one end and by an intermediate partition in the inner jacket at the other end.

3. A device according to claim 2, wherein said intermediate partition acts as a support for the needle.

4. A device according to claims 1, 2, or 3, wherein said chamber has a volume of about one third of the overall volume of the inner jacket.

5. A device according to claim 4, wherein said end wall of the housing has a connector for connection to a hypodermic needle.

6. A device according to claim 4, wherein the piston has a threaded spigot part for screw coupling with the inner jacket of the housing.

7. A device according to claim 6, wherein a sealing disc is fixed to said spigot for ensuring sealing of the container and for preventing the axial movement of the piston relative to the container before use.

8. A device according to claims 1, 2, or 3 wherein said axial bore of said stopper is closed by a diaphragm that is pierced by the needle when the housing and the container are coupled together.

9. A device according to claims 1, 2, or 3 wherein the container has diametrical dimensions such as to allow it to penetrate an annular space formed between the outer jacket and the inner jacket of the housing.

* * * * *